(12) United States Patent
Kwon et al.

(10) Patent No.: US 11,903,821 B2
(45) Date of Patent: Feb. 20, 2024

(54) INTRAOCULAR LENS EXCHANGER

(71) Applicants: THE CATHOLIC UNIVERSITY OF KOREA INDUSTRY-ACADEMIC COOPERATION FOUNDATION, Seoul (KR); Hyung Gu Kwon, Seoul (KR)

(72) Inventors: Hyung Gu Kwon, Seoul (KR); Dong Jin Chang, Seoul (KR); Young Jung Roh, Seoul (KR); Jae Hyung Han, Seongnam-si (KR)

(73) Assignees: THE CATHOLIC UNIVERSITY OF KOREA INDUSTRY-ACADEMIC COOPERATION FOUNDATION, Seoul (KR); Hyung Gu Kwon, Seoul (KR)

( * ) Notice: Subject to any disclaimer, the term of this patent is extended or adjusted under 35 U.S.C. 154(b) by 699 days.

(21) Appl. No.: 17/274,684

(22) PCT Filed: Dec. 19, 2018

(86) PCT No.: PCT/KR2018/016202
§ 371 (c)(1),
(2) Date: Mar. 9, 2021

(87) PCT Pub. No.: WO2019/221359
PCT Pub. Date: Nov. 21, 2019

(65) Prior Publication Data
US 2022/0031450 A1    Feb. 3, 2022

(30) Foreign Application Priority Data

May 17, 2018    (KR) .................. 10-2018-0056258

(51) Int. Cl.
*A61F 2/16*    (2006.01)
*A61F 9/007*   (2006.01)

(52) U.S. Cl.
CPC ............ *A61F 2/1664* (2013.01); *A61F 2/167* (2013.01); *A61F 2/1662* (2013.01); *A61F 9/007* (2013.01);
(Continued)

(58) Field of Classification Search
CPC ............ A61F 2002/1681; A61F 2/1664; A61F 2/167; A61F 2/1662; A61F 9/00709;
(Continued)

(56) References Cited

U.S. PATENT DOCUMENTS 3,991,426 A * 11/1976 Flom .................. A61F 2/1662
                                                      606/220
5,626,578 A *  5/1997 Tihon ................. A61B 18/1442
                                                       606/50

(Continued)

FOREIGN PATENT DOCUMENTS

JP    2009066178    4/2009
KR    101119307     3/2012
(Continued)

OTHER PUBLICATIONS

International Search Report—PCT/KR2018/016202 dated Mar. 11, 2019.
(Continued)

*Primary Examiner* — Darwin P Erezo
*Assistant Examiner* — Mitchell Brian Hoag
(74) *Attorney, Agent, or Firm* — CANTOR COLBURN LLP (57) ABSTRACT

Provided is an intraocular lens exchanger for moving a foldable intraocular lens (IOL), the intraocular lens exchanger including: an outer tube having a first passage formed in a forward/rearward direction; an inner tube disposed to be movable along the first passage and having a second passage formed in the forward/rearward direction;

(Continued)

and a variable tube extending from a front end of the inner tube to form a variable passage connected to the second passage, in which the variable tube has an extension part having a width that increases forward in an unconstrained state in which the variable tube is not positioned in the first passage, and the extension part is provided to be elastically deformed when the unconstrained state changes to a constrained state in which at least a part of the extension part is received in the first passage.

9 Claims, 6 Drawing Sheets

(52) U.S. Cl.
CPC ....... *A61F 9/00727* (2013.01); *A61F 9/00781* (2013.01); *A61F 2002/169053* (2015.04)

(58) Field of Classification Search
CPC .. A61F 9/00736; A61F 9/007; A61F 9/00727; A61F 9/008; A61F 9/763; A61F 9/00781; A61B 17/22031; A61B 2017/22034; A61B 2017/22035; A61B 17/00; A61B 217/22
USPC .......................................................... 623/6.12
See application file for complete search history.

(56) References Cited

U.S. PATENT DOCUMENTS

| | | | | |
|---|---|---|---|---|
| 5,716,364 A * | 2/1998 | Makker | ................ | A61F 2/1664 606/107 |
| 6,280,449 B1 * | 8/2001 | Blake | ................... | A61F 2/1664 606/107 |
| 8,439,973 B2 * | 5/2013 | Bogaert | ................. | A61F 2/167 623/6.12 |
| 2002/0082609 A1 * | 6/2002 | Green | ................... | A61F 2/1691 606/107 |
| 2003/0088253 A1 * | 5/2003 | Seil | ..................... | A61F 9/00754 606/107 |
| 2003/0176870 A1 * | 9/2003 | Ott | .......................... | A61F 2/167 606/107 |
| 2004/0015268 A1 * | 1/2004 | Kato | .................... | G05B 19/042 700/275 |
| 2008/0188877 A1 * | 8/2008 | Hickingbotham | ......................... | A61B 17/3211 606/162 |
| 2009/0292293 A1 * | 11/2009 | Bogaert | ............... | A61F 2/1664 606/107 |
| 2014/0066947 A1 * | 3/2014 | Downer | ............... | A61F 2/1678 606/107 |
| 2015/0359669 A1 * | 12/2015 | Grueebler | ............. | A61B 17/30 606/205 |

FOREIGN PATENT DOCUMENTS

| | | |
|---|---|---|
| KR | 20160033662 | 3/2016 |
| KR | 101917572 | 11/2018 |
| WO | 98037830 | 9/1998 |
| WO | 2014164847 | 10/2014 |

OTHER PUBLICATIONS

Korean Office Action—Korean Application No. 10-2018-0056258 dated Jul. 13, 2018, citing KR 2016-0033662 and JP 2009-066178.

* cited by examiner

INTRAOCULAR LENS EXCHANGER

TECHNICAL FIELD

The present application relates to an intraocular lens exchanger.

BACKGROUND ART

Cataract surgery refers to ophthalmic surgery for inserting an intraocular lens into a lenticular capsule from which a lens having opacity that interferes with the vision is removed. In the related art, an intraocular lens (PMMA IOL) having an optical part with a size of about 5 mm to 6 mm is inserted. However, because the intraocular lens (PMMA IOL) is not folded, it is necessary to make an incision in a cornea so that the incision (about 5.2 mm to 9 mm) is larger than the intraocular lens in order to insert the intraocular lens.

In contrast, a foldable intraocular lens (IOL) is currently used. Therefore, a practitioner may make an incision of about 1.8 mm to 3 mm in a cornea, hold an intraocular lens with pincers or a cartridge, fold the intraocular lens, and then insert the intraocular lens into a lenticular capsule. However, in various cases such as a case in which the inserted intraocular lens is not inserted in place or has a defect or a case in which other diseases are found and a surgical operation is performed on an eyeball, there may occur a situation in which the inserted intraocular lens needs to be withdrawn and replaced with a new intraocular lens. However, it is exceedingly difficult to withdraw the intraocular lens, which is previously unfolded (deployed) in the eyeball, through the incision as small as about 1.8 mm to 3 mm.

The background art of the present application is disclosed in Korean Patent No. 10-1119307.

DISCLOSURE

Technical Problem

The present application has been made in an effort to solve the problem in the related art, and an object of the present application is to provide an intraocular lens exchanger capable of minimizing damage to peripheral eyeball tissue by easily folding and withdrawing an intraocular lens, which is unfolded in an eyeball, without making an incision having a larger width than the intraocular lens in a situation in which the intraocular lens needs to be replaced (withdrawn and reinserted) such as a situation in which the previously inserted intraocular lens is not inserted in place or has a defect or a situation in which a surgical operation is performed on the eyeball to treat other diseases.

However, technical problems to be solved by the exemplary embodiment of the present application are not limited to the aforementioned technical problem, and other technical problems may be present.

Technical Solution

As a technical solution for achieving the above-mentioned technical object, an intraocular lens exchanger for moving a foldable intraocular lens (IOL) according to an exemplary embodiment of the present application may include: an outer tube having a first passage formed in a forward/rearward direction; an inner tube disposed to be movable along the first passage and having a second passage formed in the forward/rearward direction; and a variable tube extending from a front end of the inner tube to form a variable passage connected to the second passage, in which the variable tube has an extension part having a width that increases forward in an unconstrained state in which the variable tube is not positioned in the first passage, and the extension part is provided to be elastically deformed when the unconstrained state changes to a constrained state in which at least a part of the extension part is received in the first passage.

According to the exemplary embodiment of the present application, a width of an inner surface of a front end of the extension part may be larger than a width of the first passage in the unconstrained state.

According to the exemplary embodiment of the present application, the inner surface of the front end of the extension part may have a width equal to or larger than a radius of the intraocular lens.

According to the exemplary embodiment of the present application, the inner surface of the extension part may be formed to be linearly inclined or curvedly inclined so that a width of the inner surface of the extension part decreases rearward in the unconstrained state so that the intraocular lens is folded when the intraocular lens moves rearward in a state in which at least a part of the intraocular lens enters and comes into contact with the extension part.

According to the exemplary embodiment of the present application, an outer surface of the extension part may be formed to be linearly inclined or curvedly inclined so that a width of the outer surface of the extension part decreases rearward in the unconstrained state so that retraction of the extension part is induced when at least a part of the extension part is inserted into the first passage.

According to the exemplary embodiment of the present application, an inclination angle of each of outer and inner surfaces of a rear end of the extension part, which is defined with respect to the forward/rearward direction, may be more than 0 degree and equal to or less than 45 degrees.

According to the exemplary embodiment of the present application, the extension part may be made of a material containing polymers.

According to the exemplary embodiment of the present application, a friction reducing coating may be applied to at least a part of the inner surface of the extension part.

According to the exemplary embodiment of the present application, the extension part may include a plurality of pleated portions formed curvedly in a circumferential direction so as to be relatively extended in the circumferential direction while being unpleated in the unconstrained state in comparison with the constrained state, and to be relatively contracted in the circumferential direction while being pleated in the constrained state in comparison with the unconstrained state.

According to the exemplary embodiment of the present application, an outer surface of the outer tube may be formed to have a width that enables the outer tube to be inserted through an incision formed in an eyeball and having a size of 3 mm or less.

The technical solution is just illustrative but should not be interpreted as being intended to limit the present application. In addition to the above-mentioned exemplary embodiment, additional exemplary embodiments may be present in the drawings and the detailed description of the invention.

Advantageous Effects

According to the technical solution of the present application, the extension part, which has a width that increases forward in the unconstrained state, is inserted into the first passage to fold the intraocular lens, such that the intraocular lens in the eyeball may be folded and withdrawn. As a result, it is not necessary to make an incision having a large width corresponding to the intraocular lens, and thus it is possible to provide the intraocular lens exchanger capable of minimizing damage to peripheral eyeball tissue.

BEST MODE

Hereinafter, exemplary embodiments of the present application will be described in detail with reference to the accompanying drawings so that those with ordinary skill in the art to which the present application pertains may easily carry out the exemplary embodiments. However, the present application may be implemented in various different ways, but is not limited to the exemplary embodiments described herein. A part irrelevant to the description will be omitted in the drawings in order to clearly describe the present application, and similar constituent elements will be designated by similar reference numerals throughout the specification.

Throughout the specification of the present application, when one constituent element is referred to as being "connected to" another constituent element, one constituent element can be "directly connected to" the other constituent element, and one constituent element can also be "electrically connected to" the other element with other elements therebetween.

Throughout the specification, when one member is disposed "on", "at an upper side of", "at an upper end of", "below", "at a lower side of", or "at a lower end of" another member in the present specification of the present application, this includes not only a case where the one member is brought into contact with another member, but also a case where still another member is present between the two members.

Throughout the specification of the present application, unless explicitly described to the contrary, the word "comprise" or "include" and variations, such as "comprises", "comprising", "includes" or "including", will be understood to imply the inclusion of stated constituent elements, not the exclusion of any other constituent elements.

In addition, the terms (a front side, a front end, a rear side, a rear end, etc.) relevant to the direction or the position in the exemplary embodiment of the present application are set based on the arranged states of the respective components illustrated in the drawings. For example, when viewed in FIGS. 2A and 2B, a side generally positioned in the direction of 12 o'clock may be the front side, an end generally directed in the direction of 12 o'clock may be the front end, a side generally positioned in the direction of 6 o'clock may be the rear side, and an end generally directed in the direction of 6 o'clock may be the rear end.

The present application relates to an intraocular lens (IOL) exchanger.

Hereinafter, an intraocular lens exchanger according to an exemplary embodiment of the present application (hereinafter, referred to as 'the present intraocular lens exchanger') will be described.

The present intraocular lens exchanger 1 may be used for an ophthalmic surgery for inserting an intraocular lens into a lenticular capsule from which a lens having opacity, which interferes with the vision, is removed through an incision 11 made by cutting a cornea 10 or for an ophthalmic surgery for withdrawing the previously inserted intraocular lens. There is increasing frequency of ophthalmic surgeries for inserting multifocal intraocular lenses. However, in a case in which the power of the multifocal intraocular lens is not accurate after the ophthalmic surgery, there is a high likelihood that the intraocular lens inserted (into a patient who has undergone LASIK surgery, for example) needs to be withdrawn and then a new intraocular lens needs to be inserted again. Therefore, it can be said that there is a great need for applying the present intraocular lens exchanger 1 capable of easily withdrawing the previously inserted multifocal intraocular lens by allowing the previously inserted multifocal intraocular lens to be folded, and capable of inserting a new multifocal intraocular lens.

Figure 1:
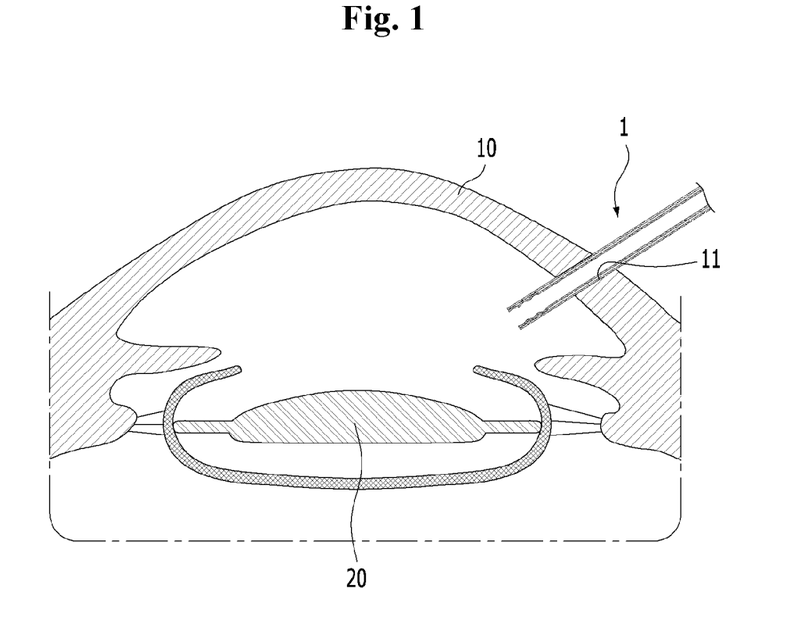
FIG. 1 is a view schematically illustrating a state in which an intraocular lens exchanger according to an exemplary embodiment of the present application is inserted into a cornea through an incision.
Figure 2A:
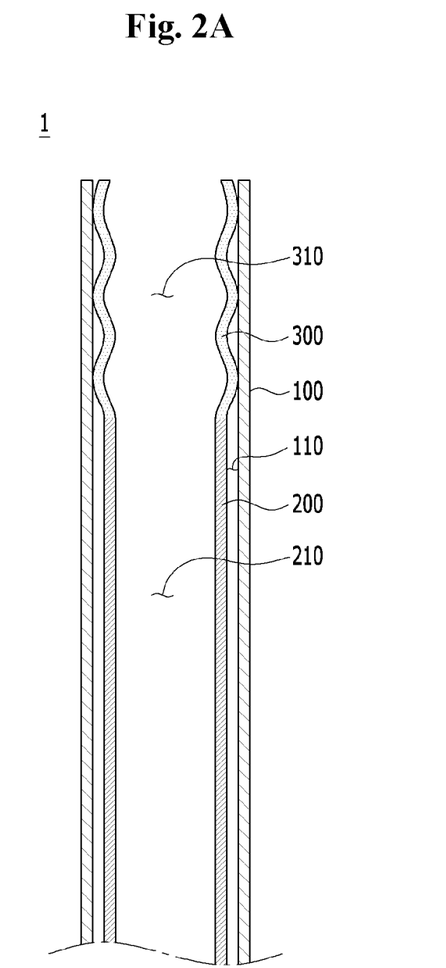
FIG. 2A is a cross-sectional view schematically illustrating a constrained state in which a variable tube is received in a first passage.
Figure 2B:
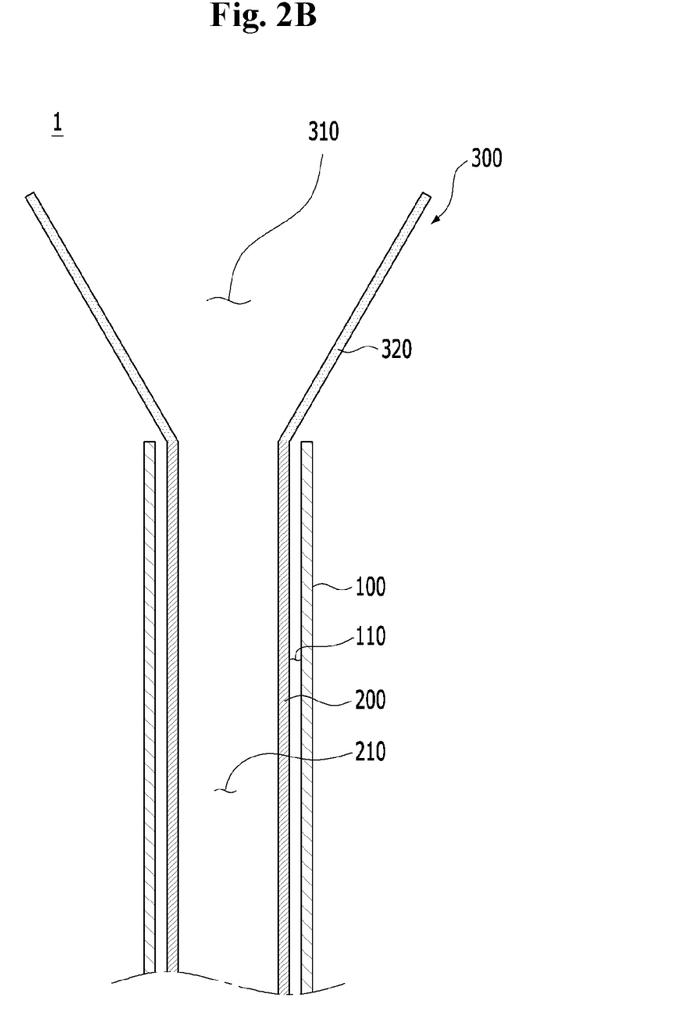
FIG. 2B is a cross-sectional view schematically illustrating an unconstrained state in which the variable tube is not positioned in the first passage.

FIG. 1 is a view schematically illustrating a state in which the present intraocular lens exchanger is inserted into the cornea through the incision. In addition, FIG. 2A is a cross-sectional view schematically illustrating a constrained state in which a variable tube is received in a first passage, and FIG. 2B is a cross-sectional view schematically illustrating an unconstrained state in which the variable tube is not positioned in the first passage. For reference, FIG. 2A illustrates a state in which a portion of the variable tube is deformed in a wave shape so as to be distinguished from a portion of an inner tube, and the variable tube may of course be variably and elastically deformed in various shapes including the wave shape. For example, an example of the elastic deformation of the variable tube may be understood with reference to FIG. 4.

Referring to FIGS. 1 and 2A, the present intraocular lens exchanger 1 may include an outer tube 100 having a first passage 110 formed in a forward/rearward direction. The outer tube 100 may be inserted into an eyeball through the incision 11. For reference, in the present application, the direction in which the outer tube 100 is inserted into the eyeball is defined as the forward direction. The outer tube 100 to be inserted into the eyeball may be made of a material harmless to a human body. As an example, the outer tube 100 may be made of, but not limited only to, a material containing at least one of tungsten, stainless, titanium, and silicone having high hardness. The outer tube 100 may be made of various metal materials used for implants, ceramic materials, or various materials harmless to a human body which is to be developed in the future. In addition, referring to FIGS. 1 and 2A, the outer tube 100 may be provided in the form of a cylindrical tube extending in the forward/rearward direction (longitudinal direction). The outer tube 100 may have the first passage 110 penetratively formed in the forward/rearward direction.

Since the outer tube 100 has a cross section having a circular ring shape as described above, a width of the outer tube 100 may be referred to as a diameter. Hereinafter, even though the term 'diameter' is used for the tube (the outer tube, the inner tube, the variable tube, etc.), the term 'diameter' may be understood as including a concept encompassing even the term 'width' in a case in which the tube does not have the circular ring shape. On the contrary, even though the term 'width' is used for the tube, the term 'width' may be understood as being used for a concept encompassing even the term 'diameter' (an inner diameter, an outer diameter, etc.) in the case in which the tube has a circular ring shape.

An outer surface of the outer tube 100 may be formed to have a width that enables the outer tube 100 to be inserted through the incision 11 formed in the eyeball and having a size of 3 mm or less. Referring to FIG. 1, the incision 11 formed to allow the outer tube 100 to be inserted into the cornea 10 of the eyeball may have a width of 3 mm or less, for example, about 2.2 mm so that the foldable intraocular lens (IOL) is inserted through the incision 11. The outer surface of the outer tube 100 may have a width corresponding to the width (size) of the incision 11 so that the outer tube 100 may be inserted through the incision 11. As an example, the width of the outer surface of the outer tube 100 may be set to be substantially equal to the width of the incision 11 within an error range. As another example, when taking into consideration that the incision 11 is made in the cornea 10 of the eyeball, the width of the outer surface of the outer tube 100 may be set to be larger than the width of the incision 11 within a range in which the cornea 10 is extended or contracted.

The present intraocular lens exchanger 1 may include an inner tube 200 disposed to be movable along the first passage 110 and having a second passage 210 formed in the forward/rearward direction.

Referring to FIGS. 1 and 2A, a width of an outer surface of the inner tube 200 may be smaller than a width of an inner surface of the first passage 110 so that the inner tube 200 may be inserted into the first passage 110 and moved in the first passage 110. The inner tube 200 may have a cylindrical tube shape extending in the forward/rearward direction (longitudinal direction). The inner tube 200 may have the second passage 210 penetratively formed in the forward/rearward direction. As an example, an inner surface of a front end of the inner tube 200 may have a width of about 2 mm. In addition, the inner tube 200 may be made of a material identical or similar to the material of the outer tube 100.

Referring to FIGS. 2A and 2B, the present intraocular lens exchanger 1 may include a variable tube 300 extending from the front end of the inner tube 200 so as to define a variable passage 310 connected to the second passage 210. The variable tube 300 may be manufactured such that a rear end of the variable tube 300 is connected to the front end of the inner tube 200. For example, the variable tube 300 may be integrally connected to the inner tube 200 by being bonded to the front end of the inner tube 200 by means of various bonding methods such as a bonding agent or thermal bonding. As another example, the variable tube 300 may not be mutually bonded to the inner tube 200 but may be manufactured to be continuously integrated with the inner tube 200. Since the variable tube 300 extends forward from the front end of the inner tube 200 as described above, the second passage 210 and the variable passage 310 may be connected to each other so as to communicate with each other, as illustrated in FIG. 2A. In addition, a width of a front end of the second passage 210 may correspond to a width of a rear end of the variable passage 310 so that the second passage 210 and the variable passage 310 are connected to each other. The variable tube 300 is connected to the inner tube 200 so that the variable tube 300 may move along the first passage 110 together with the inner tube 200.

In addition, a retractor 30 capable of picking up an intraocular lens 20 may be inserted into the second passage 210. The retractor 30 may be inserted into the second passage 210 and the variable passage 310 from a rear side of the second passage 210 to a front side of the variable passage 310 and may protrude toward the front end of the variable passage 310. The retractor 30 may have a width smaller than the width of the inner surface of the second passage 210 and the width of the inner surface of the variable passage 310 so that the retractor 30 may move in the forward/rearward direction along the second passage 210 and the variable passage 310, like a movement of a general endoscope. As an example, the retractor 30 may be, but not limited only to, forceps. That is, the retractor 30 may be understood broadly as a concept encompassing various units capable of picking up the intraocular lens 20 by being inserted through the second passage 210.

As an example, the movements of the inner tube 200 and the variable tube 300 in the first passage 110 may be implemented as the inner tube 200 may protrude toward the rear end of the first passage 110, the protruding inner tube 200 may be manipulated in the forward/rearward direction, and then the inner tube 200 and the variable tube 300 may move in the first passage 110, but the present application is not limited thereto.

The variable tube 300 may have an extension part 320 having a width that increases forward in an unconstrained state (see FIG. 2B) in which the variable tube 300 is not positioned in the first passage 110. As an example, referring to FIG. 2B, the extension part 320 may be understood as corresponding to the entire variable tube 300, but the present application is not limited thereto. As another example, the variable tube 300 may also include a section having a constant width maintained in the forward/rearward direction in addition to the extension part 320 having the width that increases forward in the unconstrained state. Specifically, a tube having a constant width may extend by a predetermined length (section) from the front end of the extension part 320 of the variable tube 300. As still another example, the variable tube 300 may have a section having a width that decreases forward in the unconstrained state unlike the extension part 320. Specifically, the front end of the extension part 320 of the variable tube 300 may be finished as a tube having a width (diameter), which decreases forward, extends by a predetermined length (section) from the front end of the extension part 320 of the variable tube 300. As described above, the variable tube 300 includes the extension part 320 having a width that increases forward in the unconstrained state, but the position application is not necessarily limited to the configuration in which the variable tube 300 includes only the extension part 320. As necessary, the variable tube 300 may also include an additional component connected to the front end or the rear end of the extension part 320.

Referring to FIGS. 2A and 2B, the change of the variable tube 300 from the constrained state to the unconstrained state may be performed as at least a part of the variable tube 300 protrudes forward from the first passage 110 in conjunction with a relative forward movement of the inner tube 200 with respect to the outer tube 100 like a change from FIG. 2A to FIG. 2B. As the variable tube 300 inserted into the first passage 110 in the constrained state protrudes forward from the first passage 110, the extension part 320 may be unfolded in a shape in which the width of the extension part 320 increases forward. The extension part 320, which is unfolded and deployed in the eyeball, may have a shape corresponding to a longitudinal section made by cutting, in the longitudinal direction, a funnel shape (fan shape) that may be a cylindrical shape having a longitudinal section which is cut out in the forward/rearward direction (longitudinal direction) and expands gradually in the unconstrained state.

The variable tube 300 may be elastically deformed so as to change from the unconstrained state to the constrained state in which at least a part of the extension part 320 is received in the first passage 110. In this case, the configuration in which the variable tube 300 may be elastically deformed means that the variable tube 300 may be elastically deformed by means of a combination of one or more of elastic contraction, elastic bending (bending), and elastic extension (tension). For example, the variable tube 300 may be made of a material that satisfies both a flexible (pliable) material capable of inducing elastic bending deformation and a material capable of inducing elastic extension and contraction. In addition, the variable tube 300 may have a shape that may constantly pattern and induce the elastic bending deformation and the elastic extension and contraction. As an example, referring to FIG. 4 to be described below, the variable tube 300 may be provided to have a plurality of pleats (to be folded) in a circumferential direction in the constrained state. Therefore, the elastic deformation of the variable tube 300 may be induced in a predetermined pattern while the variable tube 300 is elastically bent and elastically extended or contracted in accordance with a degree to which the variable tube 300 is pleated or unpleated. The change of the variable tube 300 from the unconstrained state to the constrained state may be performed as at least a part of the extension part 320 is retracted by elastic deformation while entering the first passage 100 in conjunction with the relative rearward movement of the inner tube 200 with respect to the outer tube 100. The extension part 320 unfolded in the unconstrained state may be retracted into the first passage 110 by being elastically folded or compressed while being pulled by the inner tube 200 when the inner tube 200 is moved rearward in the first passage 110 to change to the constrained state. After the variable tube 300 is received in the first passage 110, expansive force (elastic restoring force) of the extension part 320 of the variable tube 300 is cancelled out by reaction force applied by the inner surface of the first passage 110, such that the variable tube 300 may maintain the constrained state.

The extension part 320 may be made of a material containing polymers. The extension part 320 may be made of a material containing polymers having flexibility that enables the extension part 320 to be elastically deformed multiple times from the unconstrained state to the constrained state or elastically restored from the constrained state to the unconstrained state multiple times.

A width of the inner surface of the front end of the extension part 320 may be larger than the width of the first passage 110 in the unconstrained state. The inner surface of the variable passage 310, which corresponds to the rear end of the extension part 320, may have a width corresponding to the width of the inner surface of the second passage 210. In the state in which the entire region (section) of the extension part 320 protrudes from the tip of the first passage 110, the inner surface of the variable passage 310, which corresponds to the front end of the extension part 320, may have a width larger than the width of the first passage 110. In addition, the inner surface of the front end of the extension part 320 may be elastically deformed so as to have a width that enables the extension part 320 to be inserted into the first passage 110 when the unconstrained state is changed to the constrained state.

Figure 3A:
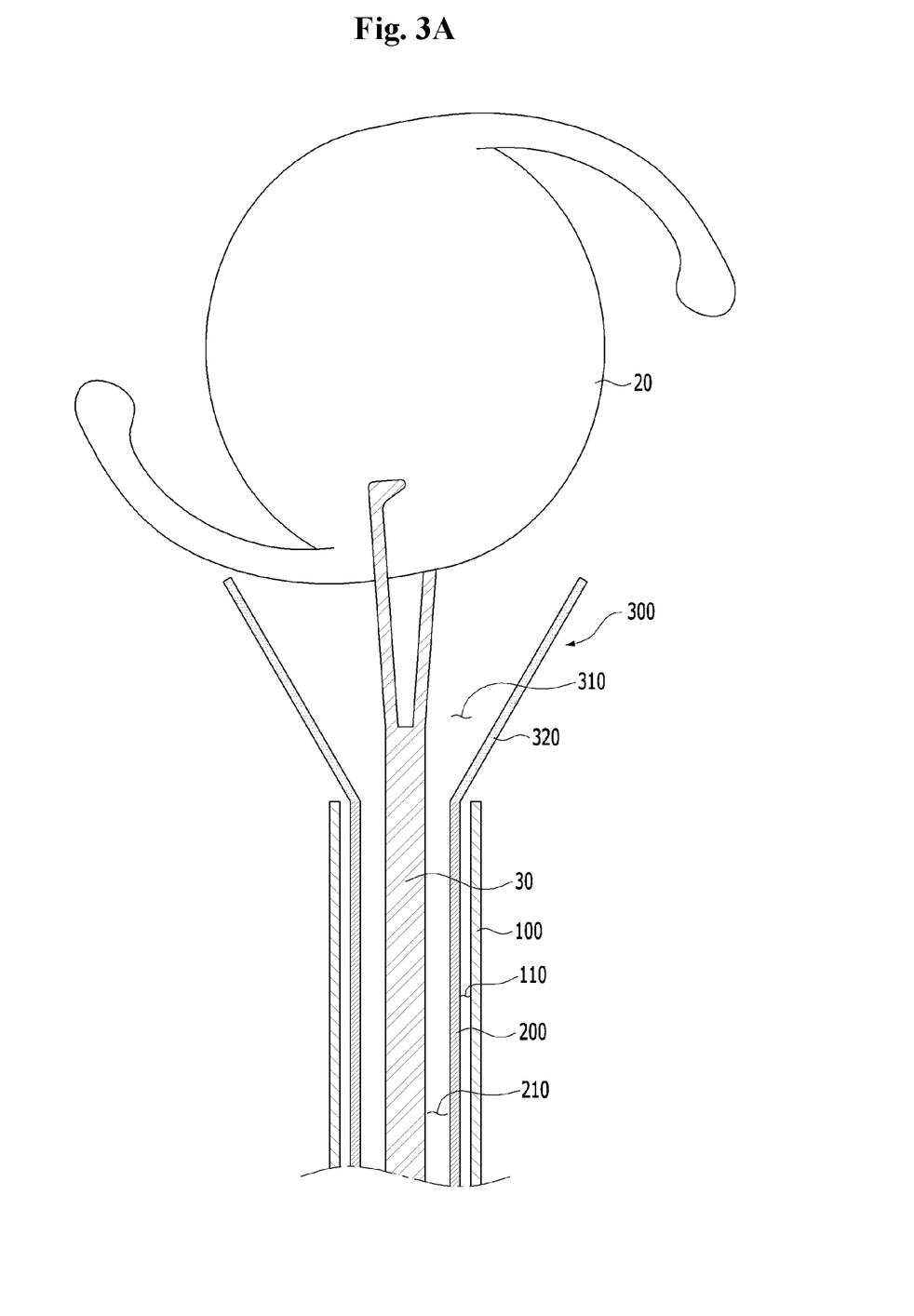
FIG. 3A is a view schematically illustrating a state in which a retractor holds an intraocular lens.
Figure 3B:
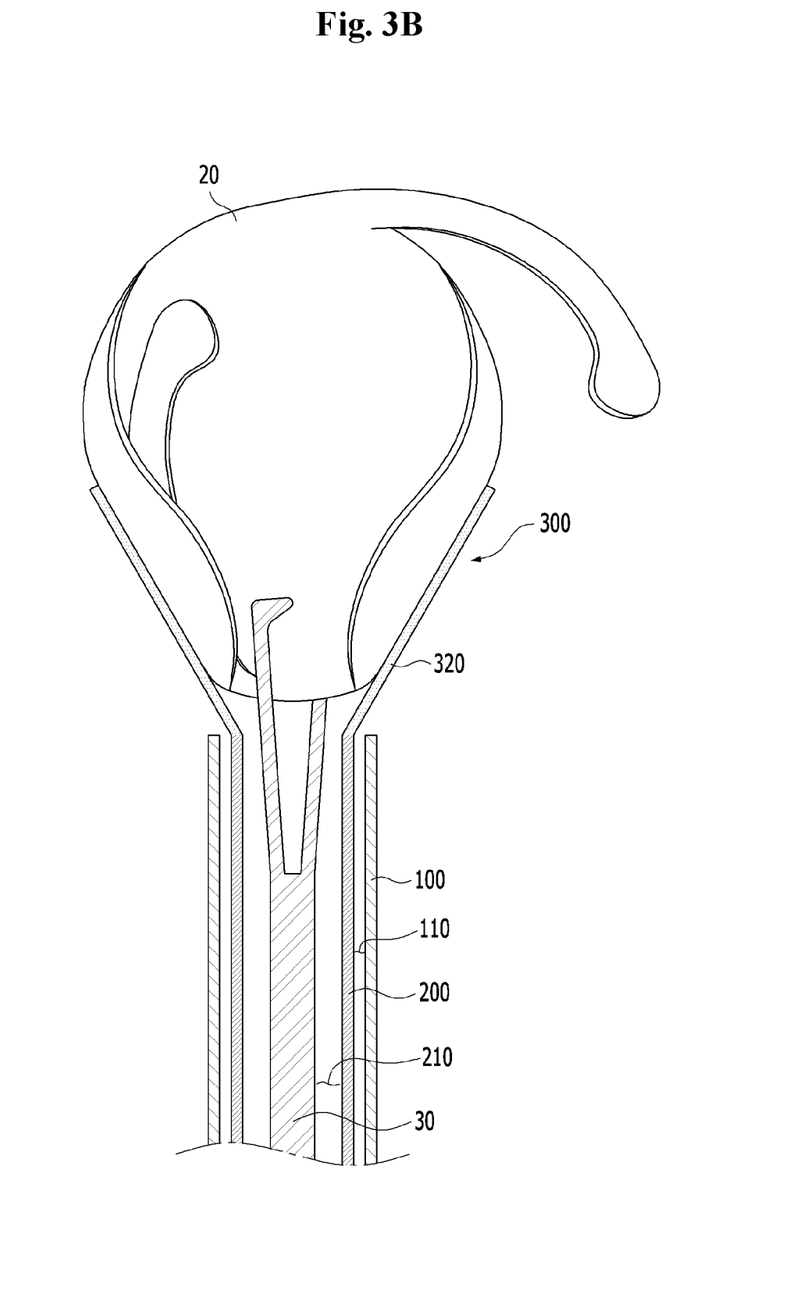
FIG. 3B is a view schematically illustrating a state in which the intraocular lens is folded when at least a part of the intraocular lens enters an extension part and moves rearward.

FIG. 3A is a view schematically illustrating a state in which the retractor holds (grasps) the intraocular lens, and FIG. 3B is a view schematically illustrating a state in which the intraocular lens is folded when at least a part of the intraocular lens enters the extension part and moves rearward. For reference, the shape of the intraocular lens is not limited only to the shape illustrated in the drawings. That is, the intraocular lens, which is an object to which the intraocular lens exchanger according to the exemplary embodiment of the present application is applied, may of course be widely interpreted as referring not only to a foldable intraocular lens already developed in the related art, but also to various foldable intraocular lenses to be developed in the future.

The inner surface of the front end of the extension part 320 may be formed to have a width equal to or larger than a radius of the intraocular lens 20. Referring to FIGS. 3A and 3B, the inner surface of the front end of the extension part 320 may be formed to have a width equal to or larger than a radius of the intraocular lens 20 so that the intraocular lens 20 may be easily and gradually folded and inserted into the second passage 210 while passing the variable passage 310 as the retractor 30 holding the foldable intraocular lens 20 moves rearward. In this case, the radius of the intraocular lens 20 means a radius based on a main body part of the intraocular lens 20 except for support members (e.g., two support members extending clockwise when viewed in FIG. 3A). In the case of the intraocular lens 20 in which the main body part of the intraocular lens 20 does not have a completely circular contour, the term 'radius' may be broadly understood as a concept of half the width. As an example, in a case in which the intraocular lens 20 has a width of 6 mm, the inner surface of the front end of the extension part 320 may be formed to have a width of 3 mm or more (e.g., about 3 mm to 4 mm).

Referring to FIGS. 3A and 3B, an outer surface of the extension part 320 may be formed to be linearly inclined or curvedly inclined so that a width of the outer surface of the extension part 320 decreases rearward in the unconstrained state so that the retraction of the extension part 320 is induced when at least a part of the extension part 320 is inserted into the first passage 110. That is, the outer surface of the extension part 320 may be linearly inclined (see FIG. 2B) or curvedly inclined so that the extension part 320 is spread (expanded) forward. For example, the outer surface of the extension part 320 may be a curved surface (an example in which a longitudinal section thereof is curvedly inclined) which is convex toward a center of the extension part 320 in order to further reduce friction that occurs when the extension part 320 initially enters the first passage 110 to change from the unconstrained state to the constrained state. In this case, the curved surface convex toward the center of the extension part 320 may mean a curved surface inclined such that a gradient of the curved surface gradually increases forward.

Meanwhile, referring to FIGS. 3A and 3B, the inner surface of the extension part 320 may be formed to be linearly inclined or curvedly inclined so that a width of the inner surface of the extension part 320 decreases rearward in the unconstrained state so that the intraocular lens 20 is folded when the intraocular lens 20 moves rearward in the state in which at least a part of the intraocular lens 20 enters and comes into contact with the extension part 320. That is, the inner surface of the extension part 320 may be linearly inclined (see FIG. 2B) or curvedly inclined so that the extension part 320 is spread (expanded) forward. For example, the inner surface of the extension part 320 may be a curved surface (an example in which a longitudinal section thereof is curvedly inclined) which is convex toward the center of the extension part 320 so that the intraocular lens 20, which is held by the retractor 30 inserted through the second passage 210 and the variable passage 310, may be more easily folded while being pulled and moved rearward. As described above, the curved surface convex toward the center of the extension part 320 may mean a curved surface inclined such that a gradient of the curved surface gradually increases forward (i.e., a curved surface inclined such that an inclination of a relatively rear side thereof is more gradual than a relatively front side thereof).

More specifically, referring to FIGS. 3A and 3B, as the retractor 30 moves rearward in the state in which the retractor 30, of which the end protrudes forward from the extension part 320 through the second passage 210 and the variable passage 310, holds the intraocular lens 20 (see FIG. 3A), the intraocular lens 20 is gradually pulled toward the second passage 210 (rearward), such that the intraocular lens 20 may be folded by the inner surface of the extension part 320 that becomes narrower rearward, as illustrated in FIG. 3B.

An inclination angle of each of the outer and inner surfaces of the rear end of the extension part 320, which is defined with respect to the forward/rearward direction, may be more than 0 degree and equal to or less than 90 degrees. More particularly, the inclination angle may be more than 0 and equal to or less than 45 degrees. The outer surface of the rear end of the extension part 320 may have an inclination with an angle of 45 degrees or less so that the variable tube 300 may more smoothly enter the first passage 110 in the outer tube 100 when the variable tube 300 moves rearward in conjunction with the inner tube 200. In addition, the inner surface of the rear end of the extension part 320 may have an inclination with an angle of 45 degrees or less so that the intraocular lens 20 may be more naturally and smoothly deformed and folded when the intraocular lens 20 is deformed and folded while passing through the extension part 320.

In addition, a friction reducing coating may be applied to at least a part of the inner surface of the extension part 320. The friction reducing coating enables the intraocular lens 20 to be more smoothly folded (guided) by the inner surface of the extension part 320 in conjunction with the rearward movement of the retractor that holds the intraocular lens 20.

In addition, a flexible frame structure, which is elastically bent well, may be provided at the front end of the variable tube 300 or the front end of the extension part 320. The flexible frame structure may be provided in the form of a loop extending along a circumference of the front end and configured as a thin flexible wire. The flexible frame structure may have an original shape in the unconstrained state and have a shape bent and deformed corresponding to the internal space of the second passage in the constrained state. The flexible frame structure enables the variable tube 300 to be quickly and elastically restored to be closer to the original shape when the constrained state changes to the unconstrained state. As an example, the flexible frame structure may be embedded in the front end of the variable tube 300 or the front end of the extension part 320, but the present application is not limited thereto. In addition, the flexible frame structure may be made of a material harmless to a human body, or the flexible frame structure may be coated with a material harmless to a human body.

A process (operation) of withdrawing the intraocular lens using the present intraocular lens exchanger 1 will be described with reference to the drawings, as an example.

Referring to FIG. 1, first, the incision 11 having a size of approximately 3 mm or less is made in the cornea 10, and the present intraocular lens exchanger 1 having the variable tube 300 in the constrained state is inserted through the incision 11. When the inner tube 200 is moved forward (in the direction of 12 o'clock based on FIG. 2B) in the state in which the present intraocular lens exchanger 1 is inserted through the incision 11, the variable tube 300 connected to the inner tube 200 is also moved forward in conjunction with the inner tube 200, and the variable tube 300 changes to the unconstrained state as the extension part 320 is expanded and deployed, as illustrated in FIG. 2B. Next, the retractor 30 is inserted through the second passage 210 of the inner tube 200 and the variable passage 310 of the variable tube 300, and the retractor 30 holds the intraocular lens 20 positioned in the eyeball, as illustrated in FIG. 3A. Next, as illustrated in FIG. 3B, as the retractor 30 is moved rearward (in the direction of 6 o'clock based on FIG. 3B) in the state in which the retractor 30 holds the intraocular lens 20, the intraocular lens 20 is also gradually pulled and moved toward the second passage 210 and enters the extension part 320, and the intraocular lens 20 is folded by the inner surface of the extension part 320 which becomes narrower rearward. Next, the folded intraocular lens 20 is inserted into the second passage 210 and gradually moves rearward, such that the intraocular lens 20 held by the retractor 30 is withdrawn as the retractor 30 comes out of the second passage 210. Next, when the inner tube 200 is moved rearward (in the direction of 6 o'clock based on FIG. 2A), the variable tube 300 connected to the inner tube 200 is also moved rearward in conjunction with the inner tube 200, and the variable tube 300 is received in the first passage 110 and moved rearward, as illustrated in FIG. 2A, such that the inner tube 200 and the variable tube 300 are removed from the first passage 110.

As another example, the intraocular lens 20 may be folded as the extension part 320 of the variable tube 300 is elastically deformed while being gradually inserted into the first passage 110, such that the intraocular lens 20, which is positioned to be in contact with the extension part 320, may also be folded in conjunction with the elastic deformation. Specifically, in the state illustrated in FIG. 3B, the retractor 30 holding the intraocular lens 20 is moved rearward in conjunction with the rearward movements of the inner tube 200 and the variable tube 300, such that the elastic deformation of the extension part 320 and the folding of the intraocular lens 20 may be simultaneously induced. On the contrary, the previous example may be an example in which the intraocular lens 20 is folded by the shape of the inner surface of the extension part 320, which has a width that decreases rearward, as only the retractor 30 holding the intraocular lens 20 moves rearward but the inner tube 200 and the variable tube 300 do not move rearward in the state (unconstrained state) illustrated in FIG. 3B. In addition, as still another example, the above-mentioned two examples are mutually compromised, such that in a state in which the inner tube 200 and the variable tube 300 are moved rearward by a predetermined distance so that at least a part of the extension part 320 is inserted into the first passage 110, the rearward movements of the inner tube 200 and the variable tube 300 and the rearward movement of the retractor 30 are appropriately combined while the retractor 30 holding the intraocular lens 20 is moved rearward in accordance with the situation in which the intraocular lens 20 is folded. As a result, the present intraocular lens exchanger 1 may be used to optimize the folding and the withdrawal of the intraocular lens 20.

In addition, the present intraocular lens exchanger 1 may of course be used not only to withdraw the intraocular lens 20 inserted into the eyeball, but also to insert the intraocular lens into the eyeball. For example, it is possible to insert the intraocular lens 20 into the eyeball by inserting a unit (e.g., forceps), which holds the folded intraocular lens 20, through the second passage 210 of the inner tube 200 and the variable passage 310 of the variable tube 300 in the unconstrained state in which the extension part 320 of the variable tube 300 is expanded and deployed, as illustrated in FIG. 2B.

Figure 4:
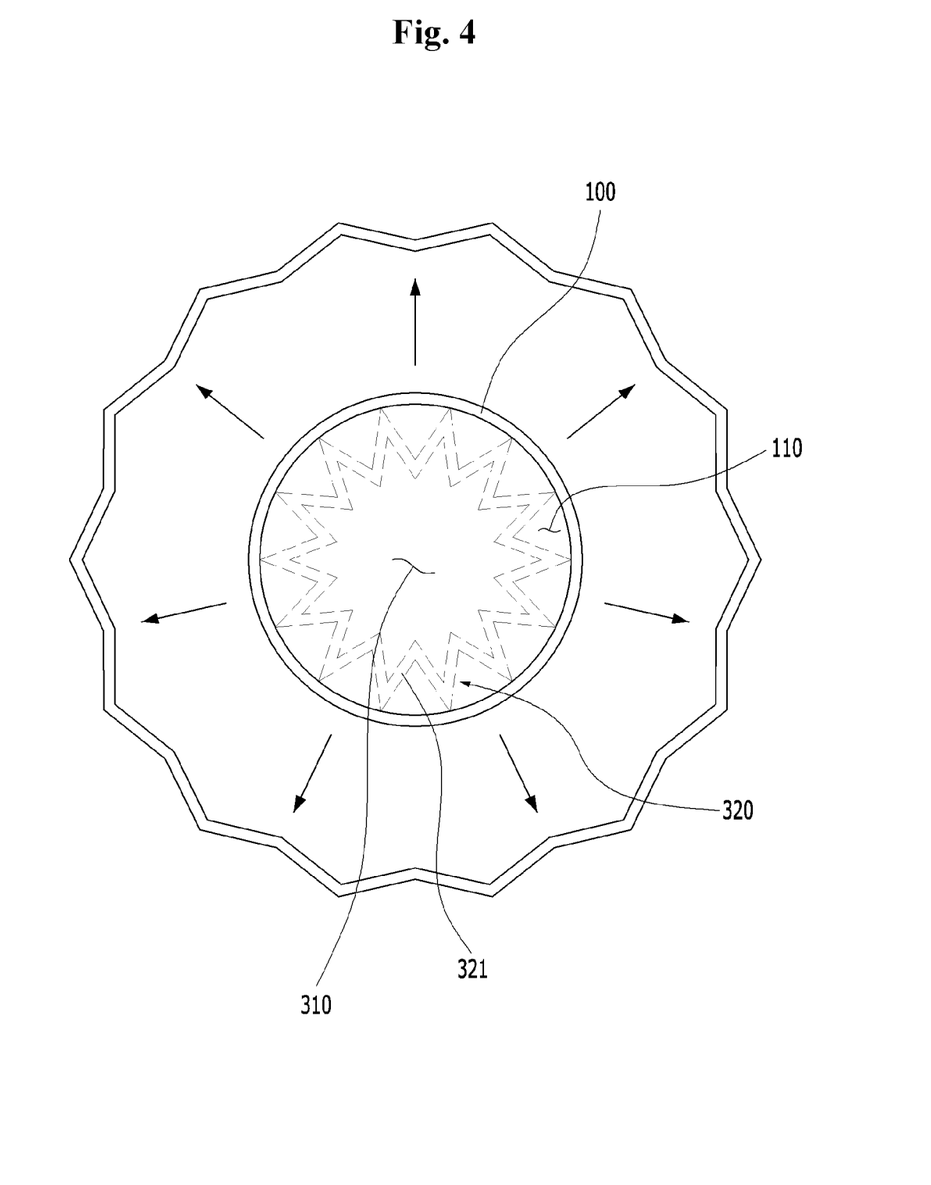
FIG. 4 is a conceptual view schematically illustrating a state in which the extension part is relatively extended in a circumferential direction while being unpleated in the unconstrained state in comparison with the constrained state.

Meanwhile, FIG. 4 is a conceptual view schematically illustrating a state in which the extension part is relatively extended in the circumferential direction while being unpleated in the unconstrained state in comparison with the constrained state.

Referring to FIG. 4, the extension part 320 may include a plurality of pleated portions 321 formed curvedly in the circumferential direction so as to be relatively extended in the circumferential direction while being unpleated in the unconstrained state in comparison with the constrained state, or to be relatively contracted in the circumferential direction while being pleated in the constrained state in comparison with the unconstrained state.

Referring to FIG. 4, the configuration in which the plurality of pleated portions 321 is formed curvedly in the circumferential direction may mean that the plurality of pleated portions 321 extends in the circumferential direction and is repeatedly curved, one or more times, inward and outward based on the circumferential direction. As an example, the pleated portion 321 may extend to be curved inward and then extend to be curved outward, or in contrast, the pleated portion 321 may extend to be curved outward and then extend to be curved inward. As illustrated in FIG. 4, the pleated portions 321 may have a shape in which a bellows shape curved in the circumferential direction of the extension part 320 extends in the longitudinal direction (a shape in which a zigzag shape repeatedly extends inward and outward in the circumferential direction). As described above, the extension part 320 may have a longitudinal section corresponding to a funnel shape that may be a cylindrical shape having a variable cross section that gradually expands, such that a width of a transverse section of the extension part 320, which has the bellows shape in the unconstrained state, may decrease rearward. However, the shape of the extension part 320 including the plurality of pleated portions 321 is not limited only to the above-mentioned shapes. For example, one or more of the plurality of pleated portions 321 may be assigned to groups, and the groups may be disposed to be spaced apart from one another at predetermined intervals in the circumferential direction of the extension part 320. Referring to FIG. 4, the extension part 320 may be received in the first passage 110 by being relatively contracted in the circumferential direction while being pleated in the constrained state in comparison with the unconstrained state. The width of the inner surface of the front end of the extension part 320 may become larger than the width of the first passage 110 as the extension part 320 is relatively extended by being gradually unpleated in the circumferential direction while protruding from the front end of the first passage 110 in the unconstrained state in comparison with the constrained state.

In addition, the pleated portion 321 may have an extension/contraction range in which the pleated portion 321 may be unpleated or pleated in order to accept the deformation so that the extension part 320 may be received in the first passage 110 in the constrained state and the extension part 320 may be expanded and unfolded in the unconstrained state.

It will be appreciated that the exemplary embodiments of the present application have been described above for purposes of illustration, and those skilled in the art may understand that the present application may be easily modified in other specific forms without changing the technical spirit or the essential features of the present application. Therefore, it should be understood that the above-described exemplary embodiments are illustrative in all aspects and do not limit the present application. For example, each component described as a single type may be carried out in a distributed manner. Likewise, components described as a distributed type can be carried out in a combined type.

The scope of the present application is represented by the claims to be described below rather than the detailed description, and it should be interpreted that the meaning and scope of the claims and all the changes or modified forms derived from the equivalent concepts thereto fall within the scope of the present application.

The invention claimed is:

1. An intraocular lens exchanger for moving a foldable intraocular lens (IOL), the intraocular lens exchanger comprising:
   an outer tube having a first passage formed in a forward/rearward direction;
   an inner tube disposed to be movable along the first passage and having a second passage formed in the forward/rearward direction; and
   a variable tube extending from a front end of the inner tube to form a variable passage connected to the second passage,
   wherein the variable tube has an extension part having a width that increases forward in an unconstrained state in which the variable tube is not positioned in the first passage, and the extension part is provided to be elastically deformed when the unconstrained state changes to a constrained state in which at least a part of the extension part is received in the first passage, and
   wherein the extension part includes a plurality pleated portions formed curvedly in a circumferential direction so as to be relatively extended in the circumferential direction while being unpleated in the unconstrained state in comparison with the constrained state, or to be relatively contracted in the circumferential direction while being pleated in the constrained state in comparison with the unconstrained state.

2. The intraocular lens exchanger of claim 1, wherein a width of an inner surface of a front end of the extension part is larger than a width of the first passage in the unconstrained state.

3. The intraocular lens exchanger of claim 2, wherein the inner surface of the front end of the extension part has a width equal to or larger than a radius of the intraocular lens.

4. The intraocular lens exchanger of claim 2, wherein the inner surface of the extension part is formed to be linearly inclined or curvedly inclined so that a width of the inner surface of the extension part decreases rearward in the unconstrained state so that the intraocular lens is folded when the intraocular lens moves rearward in a state in which at least a part of the intraocular lens enters and comes into contact with the extension part.

5. The intraocular lens exchanger of claim 4, wherein an outer surface of the extension part is formed to be linearly inclined or curvedly inclined so that a width of the outer surface of the extension part decreases rearward in the unconstrained state so that retraction of the extension part is induced when at least a part of the extension part is inserted into the first passage.

6. The intraocular lens exchanger of claim 5, wherein an inclination angle of each of outer and inner surfaces of a rear end of the extension part, which is defined with respect to the forward/rearward direction, is more than 0 degree and equal to or less than 45 degrees.

7. The intraocular lens exchanger of claim 5, wherein the extension part is made of a material containing polymers.

8. The intraocular lens exchanger of claim 7, wherein a friction reducing coating is applied to at least a part of the inner surface of the extension part.

9. The intraocular lens exchanger of claim 1, wherein an outer surface of the outer tube is formed to have a width that enables the outer tube to be inserted through an incision formed in an eyeball and having a size of 3 mm or less.

* * * * *

UNITED STATES PATENT AND TRADEMARK OFFICE
CERTIFICATE OF CORRECTION

| | | |
|---|---|---|
| PATENT NO. | : 11,903,821 B2 | Page 1 of 1 |
| APPLICATION NO. | : 17/274684 | |
| DATED | : February 20, 2024 | |
| INVENTOR(S) | : Hyung Goo Kwon et al. | |

It is certified that error appears in the above-identified patent and that said Letters Patent is hereby corrected as shown below:

On the Title Page

Items (71) Applicants, (72) Inventors, and (73) Assignees:
Hyung Gu Kwon needs to be spelled as Hyung Goo Kwon.

Signed and Sealed this
Twenty-fifth Day of November, 2025

John A. Squires
*Director of the United States Patent and Trademark Office*